United States Patent [19]

Stevenson

[11] Patent Number: 4,707,931

[45] Date of Patent: Nov. 24, 1987

[54] APPARATUS AND METHOD FOR DRYING AND SEPARATION OF MATERIAL

[75] Inventor: Barry E. Stevenson, Hamilton, New Zealand

[73] Assignee: Ministry of Agriculture & Fisheries, Wellington, New Zealand

[21] Appl. No.: 861,053

[22] Filed: May 8, 1986

[51] Int. Cl.⁴ .............................................. F26B 5/00
[52] U.S. Cl. ...................................... 34/10; 34/57 R; 34/57 E; 47/1 R; 47/58
[58] Field of Search ...................... 34/10, 57 R, 82, 85, 34/57 E; 47/1 R, 1.41, 58

[56] References Cited

U.S. PATENT DOCUMENTS 3,851,404 12/1974 Fracke et al. ........................ 34/57 E
4,530,169 7/1985 Okawara .............................. 34/57 E
4,559,719 12/1985 Dodson ................................ 34/57 E

*Primary Examiner*—Albert J. Makay
*Assistant Examiner*—David W. Westphal
*Attorney, Agent, or Firm*—Ladas & Parry

[57] ABSTRACT

The invention relates to an apparatus and method for drying anthers and separating pollen contained therein. The apparatus comprises a chamber for holding pollen bearing anthers, which has an inlet for air and an outlet from the chamber. The outlet is spaced apart from the inlet and allows for air to be drawn or passed through the inlet and to pass through the chamber to exit from the outlet. The apparatus is characterized in that air issuing from the inlet passes through means having a plurality of openings therein, said openings each being disposed at an angle to the direction of incoming air, such that the air issuing through the opening and into the chamber has a substantially twisting motion. The method comprises the steps of placing pollen bearing anthers into a chamber, and passing a twisting stream of air through said chamber, such as to disturb the anthers and release pollen therefrom.

11 Claims, 3 Drawing Figures

APPARATUS AND METHOD FOR DRYING AND SEPARATION OF MATERIAL

BACKGROUND TO THE PRESENT INVENTION

This invention relates to apparatus for drying and separating material and to a method of drying and separating material.

To enable artificial pollination of fruit producing plants, treees, vines, bushes, and the like to be carried out, it is necessary to firstly extract pollen from the flowers. This usually involves milling the flowers in order to remove the anthers therefrom and then drying the anthers and "disturbing" them in order to release the pollen stored therein. With research into artificial pollination of certain fruit bearing plants such as, for example, kiwifruit there is a need to be able to recover pollen in such a manner that the pollen has a high degree of viability.

Whilst it is possible to achieve recovery of pollen of high viability using stationary anthers, driers and subsequent pollen separation, such a method is not commercially acceptable due to the time taken to collect relatively small yields of pollen. Other known apparatus are not suitable for drying anthers for one reason or another, however, in the main, known apparatus is unsuitable because of the damage caused during the drying and/or "disturbing" process thereby resulting in pollen of low viability.

A known apparatus for the drying of materials is one which operates on a fluid bed principle whereby the material to be dried is placed within a chamber through which air is passed. Usually, the chamber is vertically orientated and the air is forced through an opening, or more usually, openings in the base of the chamber. This air flow through the chamber is ducted from the upper end thereof and passed to a separator, such as a cyclone, whereby the dried material entrained in the air is removed.

A conventional fluid bed drier is, however, unsuitable for drying anthers and separating pollen therefrom, especially anthers taken from the male flowers of a kiwifruit vine, as the antghers have long filaments that tend to entangle with each other therby causing the anthers to "nest" in lumps. Accordingly, in such a conventional fluid bed drier the air tends to blow one or two holes through the bed of anthers thereby resulting in unsatisfactory drying of the pollen.

SUMMARY OF THE PRESENT INVENTION

It is an object of one aspect of the present invention to provide an apparatus for both drying anthers and separating pollen therefrom, which permits effective drying and separating, but which avoids or at least substantially minimises, anthers becoming entangled and "nesting" into lumps.

It is a further object of one aspect of this invention to provide an apparatus for drying anthers and separating pollen therefrom, which goes at least some way towards overcoming or minimising the problems outlined above and which provides the public and industry with a useful choice.

It is a further object of one aspect of this invention to provide a method of drying anthers and separating pollen therefrom, which goes at least someway towards overcoming or minimising problems which have been encountered in the industry up until this time. It is also an object of one aspect of this invention to provide an efficient method of drying anthers and separating pollen therefrom, which provides the industry and public with a useful choice.

Other objects of this invention will become apparent from the following description.

According to one aspect of this invention there is provided apparatus for drying anthers and separating pollen contained therein, said apparatus comprising a chamber for holding pollen bearing anthers; an inlet for admission of air; an outlet from the chamber; said outlet being spaced apart from said inlet; whereby air forced or drawn through said inlet is able to pass through the chamber to exit therefrom through said outlet; characterised in that air issued from said inlet passes through means having a plurality of openings or bores therein, said openings or bores being disposed at an angle relative to the direction of incoming air, such that air issuing through said openings and into said chamber has a substantially twisting motion.

According to a further aspect of this invention there is provided a method of drying anthers and separating pollen contained therein, which comprises the steps of placing pollen bearing anthers into a chamber, and thereafter passing a twisting stream of air through said chamber so as to disturb said anthers and to release pollen therefrom.

According to a further aspect of this invention, there is provided an apparatus for drying anthers and separating pollen contained therein, comprising a chamber for holding pollen bearing anthers; an inlet for admission of air and an outlet from said chamber; characterised in that means are provided inwardly of said air inlet to impart a substantially twisting motion to air issuing into said chamber.

BRIEF DESCRIPTION OF THE ACCOMPANYING DRAWINGS

The present invention will now be described by way of example only, and with reference to the accompanying drawings, wherein.

DESCRIPTION OF THE PREFERRED EMBODIMENTS OF THE PRESENT INVENTION

The present invention will now be described by way of example only. Throughout the following description, reference will be made by way of example, to the drying and separating of pollen from anthers, and to a method of recoving pollen from pollen bearing anthers. Reference will be made by way of example, to the recovery of pollen from anthers taken from the male flower of kiwifruit vines. It should be appreciated however, that this is by way of example only, and that the apparatus and method of the present invention are equally applicable to anthers taken from other plants, bushes, trees, vines, vegetation and the like. Indeed, the present invention is applicable to any particulate matter which would normally be subjected to satisfactory drying in a standard fluid bed dryer, in which the particulate material normally binds or otherwise joins together, while in the air flow of the dryer.

Figure 1:
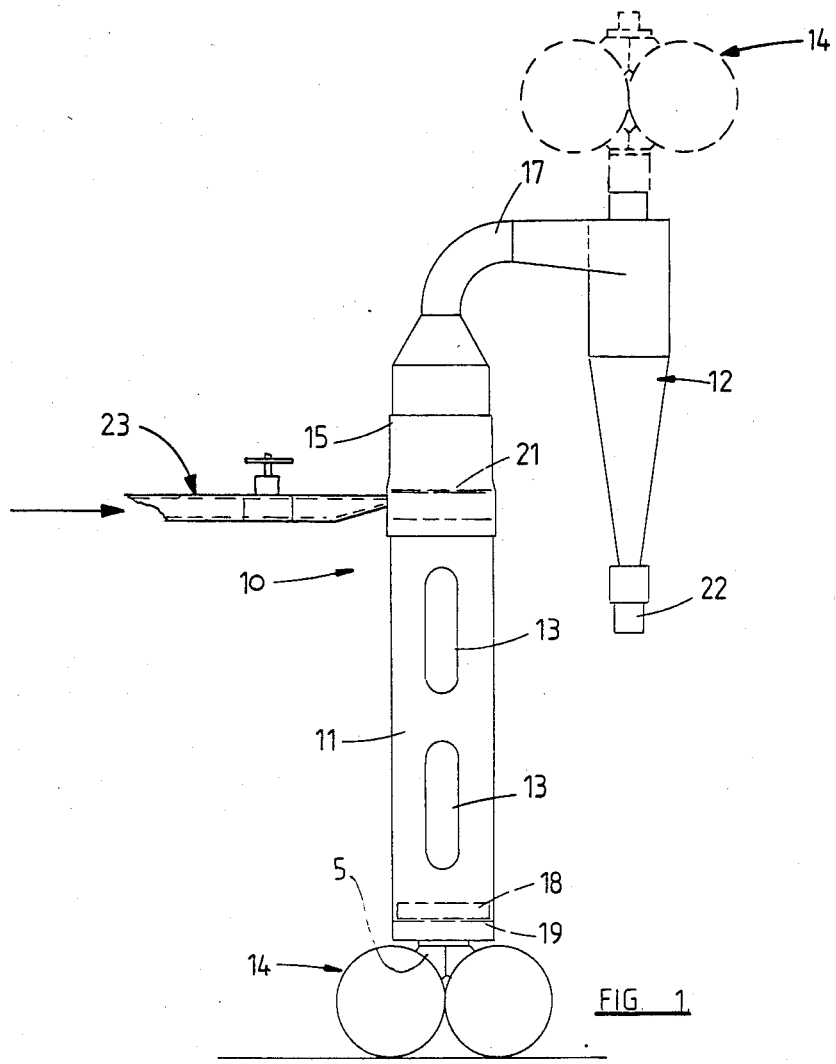
FIG. 1 is an elevational view of one embodiment of the separating apparatus according to one form of the present invention.

Referring firstly to FIG. 1 of the accompanying drawings, there is illustrated a drying apparatus 10, which includes a tower 11 connected by appropriate connecting means, to a cyclone 12. In the preferred form of the invention, the tower 11 is conveniently provided with one or more viewing windows or ports 13.

The lower end of the tower 11 is connected to an appropriate air supply, for example a multi-stage fan air supply 14, whereby air can be forced into an inlet 5 at the base of the tower 11. This is however by way of example only, and any appropriate air supply means can be provided.

In use, the air passes through the tower 11 to an outlet arrangement 15 and is then ducted, by way of ducting 17, to the cyclone 12.

In FIG. 1 of the accompanying drawings, an alternative arrangement is shown in ghosted detail, whereby an air supply 14 is located at or adjacent the air exit 12, where it draws or sucks air through an inlet 5 and through the tower 11.

Within the tower 11, spaced apart from, and preferably located above the inlet 5, an appropriate base plate 18 is provided. The base plate 18 is preferably fixedly mounted within the tower 11. It can however be movably (i.e.: rotatably) mounted if desired.

Figure 2:
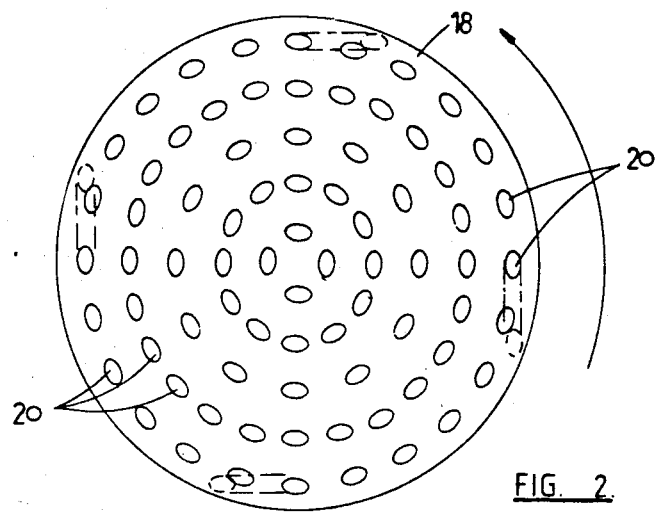
FIG. 2 is a plan view of a base plate of the apparatus according to one form of the present invention and as shown by way of example in FIG. 1.
Figure 3:
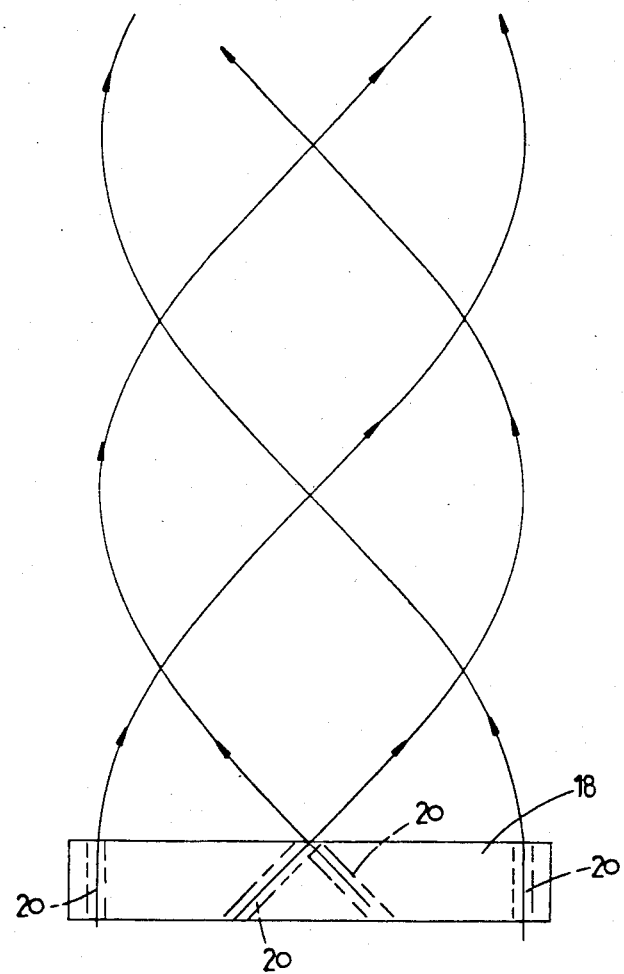
FIG. 3 is an elevational view of one aspect of the present invention showing air flow through a base plate as shown by way of example in FIG. 2 of the accompanying drawings.

Referring in particular to FIGS. 2 and 3 of the accompanying drawings, the base plate 18 which can be constructed of any appropriate material, has a plurality of air entry openings or ports 20, which preferably extend therethrough at an angle to the horizontal.

In one form of the invention, as shown for example in FIG. 1 of the accompanying drawings, a mesh filter element 19 can be provided adjacent and preferably below the base plate 18.

The base plate 18 is preferably suitably located and housed within the tower 11 and, in the preferred form of the invention, the base plate 18 is formed and designed so as to be suitable for the drying and separating of pollen from kiwifruit anthers.

In the preferred form of the invention the openings or holes 20 are formed so as to be at a typical angle or approximately 45° to the horizontal.

While in the preferred form of the invention the openings or bores 20 are substantially circular or oval when viewed in plan, and at an angle of approximately 45° to the horizontal, it should be appreciated that other angles are possible, to obtain satisfactory results from the apparatus and method.

It will be appreciated by those skilled in the art, that the size, spacing and angles of the openings 20, will be open to change and variation, in order to gain different drying and separating effects.

In the preferred form of the invention however, and as illustrated in FIGS. 2 and 3 of the accompanying drawings, the openings 20 are located in concentric circles, substantially concentric with the centre of the base plate 18 . The openings all slope or angle, for example, in the direction of the arrow shown in FIG. 2 of the drawings. It should be appreciated that this arrow also indicates the direction of twisting of the air stream which passes through the plate 18. This will be described further hereinafter.

While in the preferred form of the invention the openings or bores 20 are formed so as to slope or angle in substantially the same direction, (such as for example shown in FIG. 2 of the accompanying drawings), the openings or bores 20 may, for example, slope or be angled in different directions.

The plate 18 is preferably of such a thickness that the openings or bores 20 are elongate in formation.

The apparatus of the invention also includes a screen 21, which is preferably situated above the chamber of the tower 11 and at or adjacent the outlet 15. In the preferred form of the invention, the screen 21 is provided within the outlet arrangement 15 and is in the form of a 100 micron screen. Such a screen, while being referred to by way of example only, has been found to be particularly advantageous in separating pollen from kiwifruit anthers.

An air nozzle 23 can in the preferred form of the invention, be attached or fitted in appropriate known manner, to clean the screen. In the preferred form of the invention, means are provided whereby the nozzle 23 will provide an intermittent air stream relative to the screen 21, so that the screen 21 is cleaned intermittently.

Appropriate collection means, such as for example a pollen collection container 22, is located on or attached to the cyclone 12.

In use, kiwifruit anthers taken from the male kiwifruit flower, either in a "raw" condition or prior dried (for example in a stationary dryer), are placed into the chamber of the tower 11. Air from the air supply 14 is formed or drawn into the chamber through an opening at the base of the chamber of the tower 11. This air flow passes through the base plate 18, by way of the openings or bores 20, and due to the slanting or angled sides of the openings or bores 20, the air flow is given, or has imparted thereto, a positive "twist". This twisting air flow which is schematically illustrated by way of example only, in FIG. 3 of the drawings, grips and pulls the "nesting" anthers apart in what is an effective and yet relatively gentle manner. Thus, the method of the invention does not result in any significant pollen damage.

Pollen released from the anthers is extracted from the air stream by appropriate means; for example by using the cyclone 12. The screen 21 assists in preventing any anthers from entering into the cyclone. The pollen then exits into the container 22, for collection, storage and use.

Should a "blow-hole" in the nest of anthers begin to develope, the twisting air being applied to the anthers, will break up the anthers surrounding the hole allowing even drying to take place and continue. Because the air flow mixes the anther load continally, substantially even drying occurs throughout the full height of the load. It has been found therefore that the load does not dry in layers, which would form and result in bottom layers being overdried while top layers remained undried, or substantially undried.

In trials conducted with kiwifruit anthers, pollen having a viability ranging from between approximately 82.1% and 87.5%, (depending upon the rate of air entry into the chamber), was extracted, using the method and apparatus of the present invention.

In one form of the present invention, the air supply 14 is provided with and/or connected to, an appropriate heating arrangement, whereby air is heated prior to being forced or drawn through the inlet and into the chamber. Suitable control means or thermostat means can be associated therewith, so as to control the temperature of such air.

In a further form of the present invention, it is envisaged that the base plate 18 is in the form of a plate having a series of nozzles attached or affixed thereto. Suitable holes or bores are provided in the plate to admit air into the nozzles. The nozzles are suitably angled or directed so as to provide or impart the desired twisting motion to the air.

It is envisaged that other means may be provided to impart the substantially twisting motion to the air passing through the chamber.

The apparatus and method described hereinbefore, are in one form of the invention, particularly suitable for separating pollen from anthers which are prior dried in a separate drying arrangement, such as for example a stationary drier. This is however by way of example only.

It should be appreciated that improvements and modifications may be made to this invention without departing from the scope thereof, as defined by the appended claims.

I claim:

1. Apparatus for drying anthers and separating pollen contained therein, said apparatus comprising a chamber for holding pollen bearing anthers, an inlet for admission of air, an outlet from said chamber, said outlet being situated above said inlet, whereby air forced or drawn through said inlet is able to pass through said chamber to exit therefrom through said outlet; characterized in that air issuing from said inlet passes through a plate disposed above said inlet and having a plurality of openings extending therethrough, said openings being arranged in a series of concentric circles about the center of said plate and being slanted or disposed at an angle relative to the horizontal axis of said plate and to the direction of incoming air, such that air issuing through said openings and into said chamber has a substantially upward or vertical twisting motion.

2. Apparatus as claimed in claim 1, comprising extraction means to extract pollen from an air stream exiting from said outlet.

3. Apparatus as claimed in claim 1, wherein each of said openings is slanted or disposed at substantially the same angle and in substantially the same direction.

4. Apparatus as claimed in claim 1, wherein said plate is of a thickness such that said openings are elongate.

5. Apparatus as claimed in claim 1, wherein said openings are substantially circular in cross-section and are disposed at an angle of substantially 45 degrees to the horizontal axis of said plate.

6. Apparatus as claimed in claim 1, wherein a mesh screen is disposed below said plate.

7. Apparatus as claimed in claim 1, wherein a mesh screen is disposed adjacent the outlet from said chamber.

8. Apparatus as claimed in claim 1, wherein a mesh screen is disposed adjacent the outlet of said chamber; air cleaning means being associated with said screen.

9. Apparatus for drying anthers and separating pollen contained therein, comprising a chamber for holding pollen bearing anthers; an inlet for admission of air and an outlet from said chamber; characterized in that a plate, having a plurality of openings extending therethrough, said openings being arranged in a series of concentric circles about the center of said plate and being slanted or disposed at an angle relative to the horizontal axis of said plate, is provided inwardly of said air inlet, to impart a substantially upward or vertical twisting motion to air issuing into said chamber.

10. A method of drying anthers and separating pollen contained therein, which comprises the steps of placing pollen bearing anthers into a chamber; said chamber comprising an inlet for admission of air, an outlet from said chamber and a plate disposed above said inlet, said plate having a plurality of openings extending therethrough, said openings being arranged in a series of concentric circles about the center of said plate and being slanted or disposed at an angle relative to the horizontal axis of said plate and to the direction of incoming air; and thereafter passing a twisting stream of air through said chamber so as to disturb said anthers and release pollen therefrom.

11. A method as claimed in claim 10, comprising the further step of extracting said pollen from said air stream.

* * * * *